United States Patent
Laurent et al.

(10) Patent No.: US 12,403,030 B2
(45) Date of Patent: Sep. 2, 2025

(54) DEVICE FOR PROTECTING THE PLANTAR PADDING

(71) Applicant: MILLET INNOVATION, Loriol sur Drome (FR)

(72) Inventors: Hugo Laurent, Montélimar (FR); Thierry Fontaine, Marsanne (FR); Maria-Luisa Trepier-Le Beller, Portes les Valence (FR); Océane Martin, Loriol sur Drome (FR)

(73) Assignee: MILLET INNOVATION, Loriol sur Drome (FR)

( * ) Notice: Subject to any disclaimer, the term of this patent is extended or adjusted under 35 U.S.C. 154(b) by 328 days.

(21) Appl. No.: 17/628,007

(22) PCT Filed: Jul. 15, 2020

(86) PCT No.: PCT/IB2020/056647
§ 371 (c)(1),
(2) Date: Jan. 18, 2022

(87) PCT Pub. No.: WO2021/009691
PCT Pub. Date: Jan. 21, 2021

(65) Prior Publication Data
US 2022/0313466 A1    Oct. 6, 2022

(30) Foreign Application Priority Data
Jul. 18, 2019 (FR) ..................... 19 08129

(51) Int. Cl.
*A61F 5/01* (2006.01)
*A41D 13/06* (2006.01)
(Continued)

(52) U.S. Cl.
CPC ............ *A61F 5/0127* (2013.01); *A41D 13/06* (2013.01); *A43B 7/1405* (2013.01);
(Continued)

(58) Field of Classification Search
CPC ................ A43B 7/1405; A43B 7/1425; A43B 7/1435; A43B 7/149; A43B 7/22; A43B 17/02;
(Continued)

(56) References Cited

U.S. PATENT DOCUMENTS 10,383,380 B2 *  8/2019  Koven ............... G09B 19/0038
11,583,009 B2 *  2/2023  Yehuda ................ A41B 11/002
(Continued)

FOREIGN PATENT DOCUMENTS

FR    2957246 A1    9/2011
FR    3031037 A1    7/2016

OTHER PUBLICATIONS

Sep. 24, 2020 International Search Report issued in International Patent Application No. PCT/IB2020/056647.
Sep. 24, 2020 Written Opinion issued in International Patent Application No. PCT/IB2020/056647.

*Primary Examiner* — Aiying Zhao
(74) *Attorney, Agent, or Firm* — Oliff PLC (57) ABSTRACT

A device for protecting a plantar pad of a foot, including: a pad including a viscoelastic material, configured to be held on the skin of the plantar region, and to cover all the metatarsal heads and metatarsophalangeal joints of the foot, and an elastic strap attached to lateral edges of the pad, and including a transverse and a longitudinal portion forming a brace configured to pass between a big toe and an adjacent toe, the longitudinal portion having a distal edge fixed to a distal edge of the pad, the transverse portion having a distal edge delimiting, with the pad and a lateral edge of the longitudinal portion, an aperture for the passage of the second to fifth toes, the distal edge of the transverse portion and the lateral edge having, in a unstretched flat state, rectilinear portions forming between them an angle between 75 and 100°.

20 Claims, 4 Drawing Sheets (51) Int. Cl.
*A43B 7/1405* (2022.01)
*A43B 7/1425* (2022.01)
*A43B 7/1435* (2022.01)
*A43B 7/149* (2022.01)
*A43B 7/22* (2006.01)
*A43B 17/02* (2006.01)

(52) U.S. Cl.
CPC .......... *A43B 7/1425* (2013.01); *A43B 7/1435* (2013.01); *A43B 7/149* (2013.01); *A43B 7/22* (2013.01); *A43B 17/02* (2013.01)

(58) Field of Classification Search
CPC ............ A43B 5/12; A61F 5/0127; A61F 5/14; A61F 13/067; A41D 13/06
See application file for complete search history.

(56) References Cited

U.S. PATENT DOCUMENTS

| | | | |
|---|---|---|---|
| 2006/0179549 A1* | 8/2006 | Huggins | A43B 5/12 2/239 |
| 2006/0196078 A1* | 9/2006 | Terlizzi | A43B 7/144 36/8.3 |
| 2006/0288609 A1* | 12/2006 | Wilkenfeld | A43B 13/16 36/8.3 |
| 2008/0110045 A1* | 5/2008 | Terlizzi | A43B 7/144 36/8.3 |
| 2013/0060181 A1* | 3/2013 | Fontaine | A61F 13/064 602/30 |
| 2014/0259737 A1* | 9/2014 | Fedele Hartwell | A43B 5/12 36/8.3 |
| 2017/0347723 A1* | 12/2017 | Millet | A61F 5/019 |
| 2018/0200099 A1* | 7/2018 | Hanft | A61F 5/0111 |

* cited by examiner

DEVICE FOR PROTECTING THE PLANTAR PADDING

The present invention relates to a foot protection device, in particular for distributing the pressure on the front of the sole of the foot.

The foot has a protection layer called the "plantar pad", which can withstand up to eight times the body weight. The plantar pad distributes the mechanical load imposed by the body weight on the metatarsals. However, many people suffer from overheating, calluses or pain linked to the inevitable wear of the natural plantar pad with age, which no longer plays its load distribution role as effectively. As people age, the plantar pad tends to become thinner and harder. The foot can also suffer from skin disorders (irritations, cracks, plantar warts . . . ).

To relieve or prevent these pains and/or disorders, it is known to place a pad in a viscoelastic material chosen to distribute the loads under the metatarsal heads and/or under the metatarsophalangeal joints, in particular to avoid the formation of local hyperkeratosis, generally called calluses. To make such a pad, it is also known to use a polymer gel-based insert, such as silicone gel or hydrogel, to provide a substitute function for the plantar pad. Thus, such an insert, a few square centimeters in size, can be made from a PDMS (polydimethylsiloxane) silicone gel composition, for example marketed by the applicant under the name Epithélium 26®. Patent FR 2 712 487 discloses such a silicone gel with properties similar to those of the plantar pad used for the prevention of hyper-pressure pathologies occurring essentially on or under the feet.

The present invention more particularly aims at protecting the plantar pad in the region of the metatarsal heads and to compensate for deterioration of that region by providing a distribution of the pressure induced by the weight of the human body over the metatarsal heads. However, the presence of a pad under the metatarsal heads may disturb the user's posture and balance when walking. Indeed, the balance in the standing position results from the permanent integration of data coming from three receptor systems, namely the visual system, the proprioceptive system, and the vestibular system.

The visual system (position relative to the environment) and the vestibular system (detection of rotational and linear accelerations of the head in space by an organ in the ear) should not be affected by the presence of a pad under the foot. This is not the case for the proprioceptive system, because the perception of the ground by the cutaneous and deep mechanoreceptors is attenuated by the interposition of the pad. However, the consideration of the signals coming from these sensors leads to muscular reactions aiming to make the conscious or non-conscious sensation of imbalance disappear. These muscular reactions can be at the origin of pathologies that may be temporary, such as cramps, or of longer duration such as tendinitis in the global kinematics of the body.

The applicant has developed and commercialized a pad adapted to seniors with a worn plantar pad (thinner and harder). This pad forms an extra thickness under the foot of more than 3 mm for a viscoelastic material thickness of 2.2 mm. This pad fulfils its function of compensating the wear of the plantar pad. However, the way in which the pad is held on the foot, the bulk and the comfort associated with wearing the pad in a shoe, deserve to be improved.

It may therefore be desirable to provide a pad with a pressure distribution function, associated with holding means capable of keeping the pad comfortably in place on the foot, without causing postural instability of the user. It may therefore also be desirable that the pad and the holding means are not too bulky in order to be compatible with wearing shoes without introducing discomfort. It may also be desirable that the pad does not cause injury, particularly to the toes, nor skin reactions. It may also be desirable that both the pad and the holding means can be used for several months and can be easily manufactured.

Embodiments relate to a device for protecting a plantar pad of a foot, comprising: a pad including a viscoelastic material, configured to be held on the skin of the plantar region, and to cover all the metatarsal heads and metatarsophalangeal joints of the foot, and an elastic strap attached to lateral edges of the pad, and comprising a transverse portion and a longitudinal portion forming a brace configured to pass between a big toe and an adjacent toe of the foot, the longitudinal portion having a distal edge fixed to a distal edge of the pad, the transverse portion having a distal edge delimiting, with the pad and a lateral edge of the longitudinal portion, an aperture for the passage of the second to fifth toes, the distal edge of the transverse portion and the lateral edge having, in a unstretched flat state, rectilinear portions forming between them an angle between 75 and 100°, the lateral edge having a length between 40 and 60% of the length of the distal edge of the transverse portion, the length of the distal edge of the transverse portion being between 55 and 65% of the length of the transverse portion.

According to an embodiment, the distal edge of the longitudinal portion is attached to the distal edge of the pad after rotating by an angle between 80 and 100° in the plane of the pad.

According to an embodiment, the distal edge of the longitudinal portion and the distal edge of the pad form an angle between 70° and 90° with each other, before fixing the longitudinal portion to the pad.

According to an embodiment, the longitudinal portion has at its distal end a width of 1.5 cm±20%.

According to an embodiment, the pad comprises an outer fabric piece joined with an inner fabric piece to form a pocket in which an insert is housed.

According to an embodiment, the outer fabric piece has a thickness between 0.5 and 0.8 mm, and the inner fabric piece has a thickness between 0.1 and 0.5 mm.

According to an embodiment, the insert is bonded to the outer fabric piece.

According to an embodiment, the insert has a planar base and studs formed on an upper side of the planar base.

According to an embodiment, the flat base has a thickness between 1.4 and 2 mm, and the studs extend over a height above the flat base between 1.3 and 1.7 mm and have a total volume per unit of area equivalent to that of a flat layer having ⅓ of the height, to within ±10%.

According to an embodiment, the studs have a spherical cap shape with a diameter of 4 mm±0.2 mm, and are spaced apart from each other in 0°, 60° and 120° directions by a distance of 5 mm to within ±0.2 mm.

According to an embodiment, the viscoelastic material is based on a polydimethylsiloxane silicone gel composition.

Non-limiting examples of embodiments of the invention will be described in the following, in relation to the attached drawings, among which.

Figure 1:
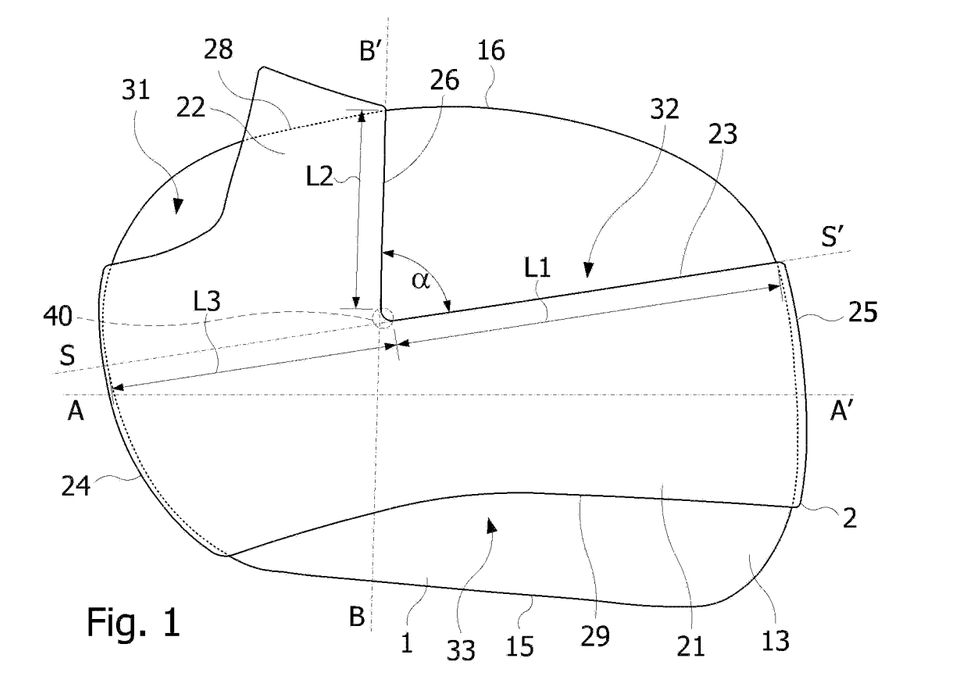
FIG. 1 schematically shows a top view of a device for protecting the plantar pad in the region of the metatarsal heads.
Figure 2:
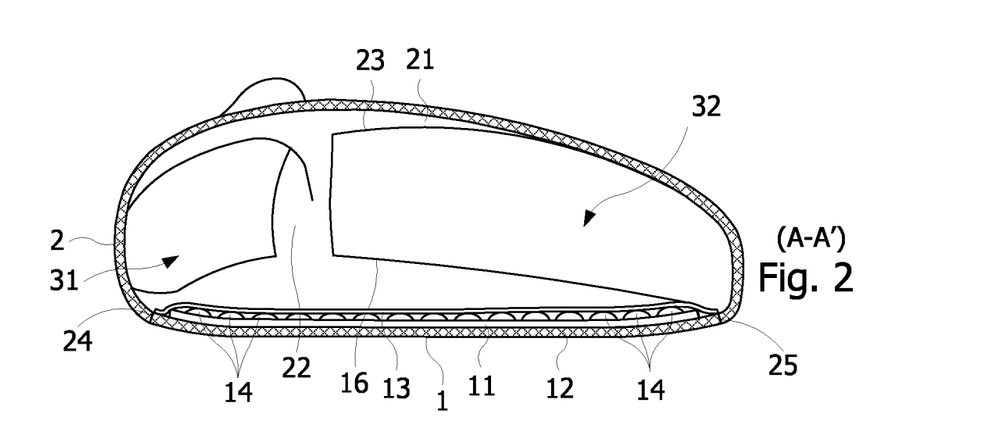
FIG. 2 is a cross-sectional view of the protection device, in the plane AA' shown in FIG. 1.

FIGS. 1 and 2 show a foot protection device according to an embodiment. The protection device comprises a pad 1 and an elastic strap 2 having a transverse portion 21 attached to the pad 1 along two opposite side edges 24, 25 of the pad 1. The assembly of the pad 1 and the strap 2 thus forms a sleeve with two opposite openings 31-32, 33, fitted to slightly constrict the front of the foot. The strap 2 is also attached to the pad 1 by a brace 22 integral with the strap 2, and attached to a distal longitudinal edge 16 of the pad. The brace 22 thus defines two distal openings 31, 32, the opening 31 being provided for the passage of the big toe of the foot, and the opening 32 being provided for the passage of the other toes. The lateral and distal attachments of the strap 2 to the pad 1 are, for example, provided by seams.

According to an embodiment, the strap 2 is made of an elastic fabric, for example a run-resistant fabric, and has a thickness between 0.5 and 1 mm, for example of the order of 0.6 mm.

According to an embodiment, the opening 32 is delimited on the side of the strap 2 by two edges having straight portions, namely a transverse edge 23 of length L1, formed by the transverse portion 21, and a longitudinal edge 26 of length L2, formed by the brace 22. The edges 23, 26 are connected to each other by a curved edge in a region 40 of the strap 2. The edge 23 extends along an axis SS' and the edge 26 extends along an axis BB', the axis BB' forming an angle $\alpha$ with respect to the axis SS'. According to an embodiment, the angle $\alpha$ is between 75 and 100°, the ratio L2/L1 is between 40 and 60%, preferably between 45 and 55%, and the curved edge has a radius of curvature of less than 1 cm.

The pad 1 comprises an insert 11 made of a viscoelastic material adapted to provide a pressure distribution function (FIG. 2). According to an embodiment, the insert 11 is housed in a pocket formed by an outer fabric piece 12 joined with an inner fabric piece 13. The shape and dimensions of the pocket may be precisely matched to those of the insert 11. The insert 11 may be bonded over its entire surface to one of the two fabric pieces 12, 13, for example the outer fabric piece 12. The outer fabric piece 12 and the inner fabric piece 13 may be resilient and have a thickness between 0.5 and 0.8 mm, for example of the order of 0.6 mm. According to an embodiment, the inner fabric piece 13 has a smaller thickness, for example between 0.1 and 0.5 mm, for example in the order of 0.2 mm. The fabric pieces 12, 13 may be joined to each other along the periphery of the insert 11, for example by a seam.

According to an embodiment, the insert 11 is made of a viscoelastic polymer gel, for example a silicone gel. Thus, the insert 11 may, for example, be made of PDMS (polydimethylsiloxane) having a shore 00 hardness between 10 and 40 (equivalent to a shore A hardness of 05), and preferably 17.

The insert 11 may have a thickness between 1.7 and 3.5 mm, for example of the order of 1.8 mm. In this way, the total thickness of the protection device under the foot may be at least 2.5 mm. Under these conditions of thickness and hardness of the insert 11 and of the thickness of its fabric envelope (12, 13), the insert 11 can ensure effective protection of the plantar pad, without disturbing the postural stability of the user, while occupying a minimum space in the footwear.

Figure 3:
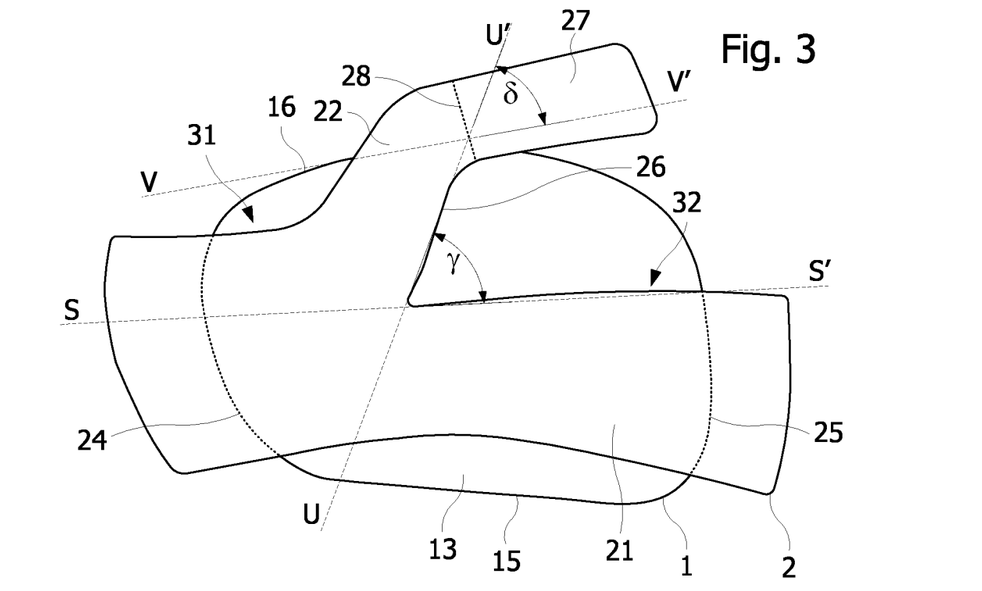
FIG. 3 is a top view of the protection device when attaching a strap coming over the foot, before attaching a brace.
Figure 4:
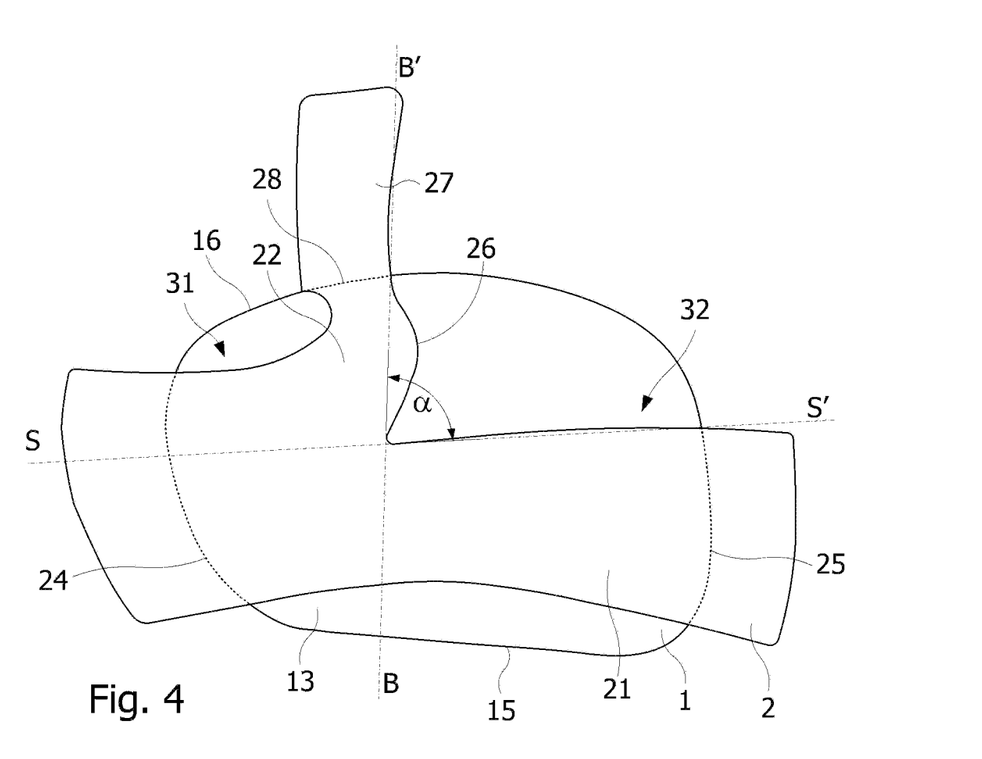
FIG. 4 is a top view of the protection device while attaching the strap, after the brace is attached, FIG. 5 schematically shows a foot fitted with the protection device.

FIGS. 3 and 4 show the shape of the strap 2, flat in FIG. 3 and sewn to the pad 1 in FIG. 4. In FIG. 3, the strap 2 is laid flat on the pad 1 and then attached to the pad 1 in this position along the side edges 24, 25 of the pad 1 (FIG. 4), without being stretched, so that the length of the strap 2 at rest, after attachment, between the side edges 24, 25, corresponds substantially (within 10%) to the width of the pad 1 between these edges. In this position, the side edge 26 of the brace 22 extends in a direction UU' at an angle $\gamma$ with the direction SS' of the edge 23 of the transverse portion 21 on the side of opening 32. The brace 22 has a distal portion 27 extending substantially in the direction of the transverse portion 21 of the strap 2. The distal portion 27 of the brace 22 extends in a direction VV' at an angle $\partial$ with the direction UU', such that the direction VV' is at an angle $\gamma-\partial$ with the direction SS'. In the example shown in FIG. 3, the angle $\gamma$ is between 60° and 85°, and the angle $\gamma-\partial$ is in the range of 0 to 20°.

As illustrated in FIGS. 3 and 4, the distal portion 27 of the brace 22 is secured flat, without being stretched, to the distal edge 16 of the pad 1 by a securing line 28 extending substantially perpendicularly (within ±10°) to the distal portion 27 (direction VV') and extending from a point of intersection between the lateral edge 26 of the brace 22 at rest and the distal edge 16 of the pad 1 (FIG. 3). The brace 22 is secured to the distal edge 16 of the pad 1 by rotating the brace 22 in the plane of the pad 1 so as to increase the angle $\gamma$ between the axes SS' and UU' to reach the angle $\alpha$, and thereby cause the axis UU' to coincide with the axis BB' (FIG. 1), and rotating the attachment line 28 on the brace 22 about the point of intersection between the side edge 26 of the brace and the distal edge 16 of the pad 1, to coincide with the distal edge 16 of the pad 1. In this way, the brace 22 is fixed to the pad 1 forming a camber, keeping the opening 31 open, the size of this camber being determined by the amplitude of these two rotations. Under these conditions, the lateral edge 26 of the brace 22, on the opening side 32, extends along the axis BB' forming the angle $\alpha$ with the axis SS'. Considering that the distal edge 16 at the location of the attachment of the brace 22 is substantially parallel to the axis SS', the angle of rotation of the attachment line 28 is substantially equal to 90°-($\gamma$-$\delta$6), i.e. between 70° and 90°.

Figure 5:
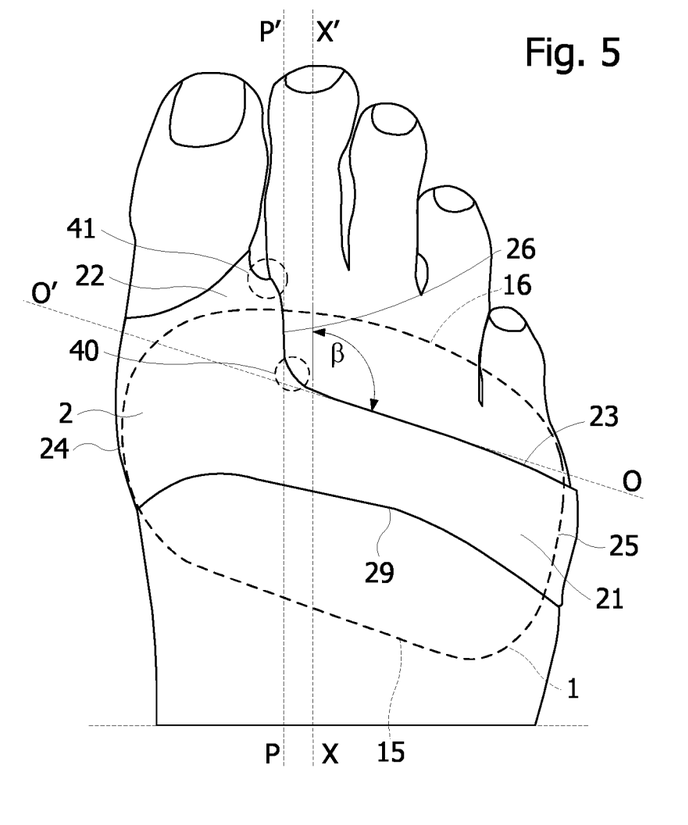

As illustrated in FIG. 5 showing the protection device fitted on a foot, the shape and dimensions of the pad 1 (and thus of the insert 11) are intended to cover the entirety of the metatarsal heads and metatarsophalangeal joints of the foot, and where appropriate, part of one or both lateral edges of the foot. The pad 1 is intended to be fitted on the foot so that its distal edge 16 substantially coincides with a line passing through the base of the toes in the case of an Egyptian foot. The edge 23 of the opening 32 belonging to the transverse portion 21 of the strap 2, extends along an axis OO', and the edge 26 of the opening 32 belonging to the brace 22, extends along an axis PP'. The edge 26 of the brace 22 on the side of opening 32 passes through the region 41 of the commissure between the big toe and the second toe. In addition, the camber surrounds the big toe.

When the support device is correctly positioned in rotation around the foot (around the XX' axis), the PP' axis is substantially parallel (to within ±10°, depending on the morphology of the foot) to the XX' longitudinal axis of the foot, passing through the center of the heel and the middle of the end of the second toe. Furthermore, when the support device is correctly positioned along the axis XX' of the foot, the axis PP' forms an angle β with the axis OO' between 100 and 120°, depending on the morphology of the foot. In the example shown in FIG. 5, the angle β is approximately 110°.

When these conditions for proper placement of the support device on the foot are met, the shape and arrangement of the strap 22 described above, avoids applying tension between the lateral region of the foot on the side of the little toe (attachment line 25) and the region 41 of the commissure between the big toe and the second toe. It has been found that these tensions would tend to promote forward movement of the device and generate uncomfortable shearing on the commissure between the big toe and the second toe. The elimination of these tensions therefore minimizes the risk of displacement and thus misplacement of the support device during use, and helps to improve the comfort of the support device around the big toe.

In addition, the curvature of the brace 22 around the big toe allows the fabric to adhere to the medial edge of the first metatarsophalangeal joint without placing significant tension on the region 41 of the commissure with the second toe. This arrangement also helps to improve the comfort of the support device around the big toe.

Compared to a strap without curvature and with a reduced or absent length L2, the characteristics of the strap 22 also offer a significant stretching capacity on the part of the strap corresponding to the passage on the commissure between the big toe and the second toe. The presence of the strap 22 is therefore less felt by the user, which allows for long term use of the support device without producing discomfort for the user. The daily time of use of the support device is thus increased.

According to an embodiment, the brace 22 has a relatively large width—about 1.5 cm (more or less 20%)—along the seam 28. This large width, which is permitted by the formation of the camber, further reduces the risk of shearing that may be caused by the strap 22 on the commissure between the first and second toes (region 41).

Figure 6:
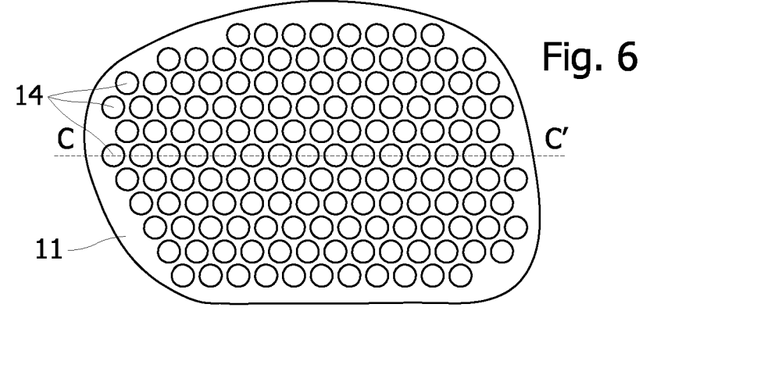
FIG. 6 is a top view of a pad housed in the brace.
Figure 7:
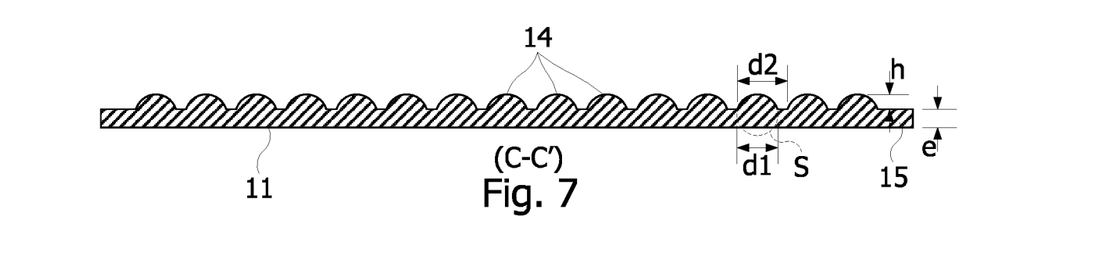
FIG. 7 is a cross-sectional view of the pad of FIG. 7, along a plane CC' shown in FIG. 6.

FIGS. 6 and 7 show an insert 11 according to an embodiment. The upper face (foot-side) of the insert 11 has a flat base 15 of a thickness e, over which studs 14 are distributed. In the example of FIGS. 6 and 7, the studs 14 have a shape of a spherical cap S of diameter d1 and are regularly distributed over the base 15 of the insert 11. The studs 14 protrude by a height h above the base 15 of the insert 11 and are spaced apart from each other by a distance d2 along three directions at 0°, 60° and 120°. According to an embodiment, the thickness e is chosen at 1.7 mm (±0.3 mm), the height h is chosen at 1.5 mm (±0.2 mm), the diameter d1 of the spheres is chosen at 4 mm (±0.2 mm), and the distance d2 between the studs 14 is chosen at 5 mm (±0.2 mm). Under these conditions, the volume of material above the flat base 15 of thickness e is divided by a factor of about 3, compared to a layer of constant thickness having the height h. In other words, this volume corresponds to that of a layer of constant thickness equal to approximately ⅓ of the height h, to within ±10%.

Figure 8:
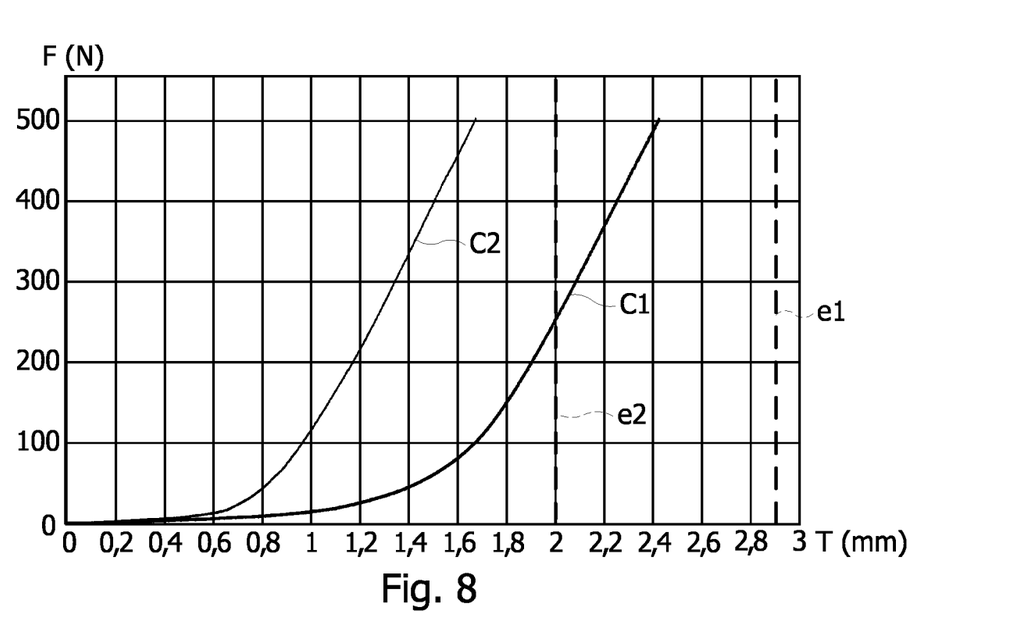
FIG. 8 shows curves illustrating a crushing property of the wafer of FIG. 6.

FIG. 8 shows curves C1, C2 of an applied force F (in N) versus a crush depth T (in mm) for different inserts. The curve C1 was obtained with insert 11 (FIG. 6), and the curve C2 was obtained with a flat insert having approximately the same volume of material per area unit as insert 11. FIG. 8 also shows the initial thicknesses e1 (=2.9 mm) of insert 11 and e2 (=2 mm) of the other insert. The curves C1 and C2 each show three phases, namely a first phase called "contact" where the crushing of the pad offers little resistance (the thickness of the pad decreases rapidly as a function of the crushing force), a second intermediate phase which starts when the crushing of the insert reaches about 1 mm for insert 11 and 0.6 mm for the other insert, when the crushing force is between a few Newtons and approximately 20 N for curves C1 and C2, and a third phase, known as the "stiffening" phase, in which the crushing of the insert increases substantially linearly and faster along the crushing force axis. During the stiffening phase, which starts at a force of about 200 N for a crushing depth of about 1.9 mm for curve C1 and at a force of about 100 N for a crushing depth of about 0.95 mm for curve C2, curves C1 and C2 have approximately the same slope. This can be explained by the fact that during this phase, the insert 11 behaves substantially like a flat plate.

In comparison with curve C2, the intermediate phase of curve C1 is thus longer and ends with an additional compression of approximately 0.95 mm. This is due to the studs 14 crushing until the space between them is filled, after they have contacted each other, and to the flat base 15 of the insert 11 being less compliant. During this intermediate phase, the crushing of the insert 11 is not proportional to the force applied to the insert. This intermediate phase provides a prolonged welcoming comfort to the pad 1 as the foot begins to compress the pad against the ground. When the force reaches 500 N during the stiffening phase, the insert 11 has a thickness of about 0.48 mm and the other insert has a thickness of about 0.33 mm. The stiffening phase does not affect postural stability and prevents excessive local development of a callus layer (keratinization) thanks to the pressure distribution provided by the pad.

When comparing the insert 11 with a flat insert having a thickness with the same pressure distribution capability, the flat insert must have a thickness greater than that e of the base 15 of the insert 11—2 mm when the base of the insert 11 has a thickness of 1.5 mm and a height h of the studs 14 of 1.4 mm. The studs 14 crush more readily than the base of the flat insert in response to loading and create a compression phase of the studs 14 occurring before a compression phase of the flat base 15, providing a compression response similar to that of a flat insert having a final substantially similar thickness (0.48 mm for insert 11, 0.33 mm for the other insert), taking into account the average weight of an adult person (500 N).

It should be noted that the studs 14 slightly penetrate the soft tissue of the plantar pad, which further reduces the thickness felt under the foot compared to a flat insert. As a result, the insert 11 has a potentially smaller footprint in the shoe than a flat insert, providing improved comfort for the user and less degradation of stability when walking. The penetration of the studs 14 into the soft tissues of the plantar pad also contributes to improving the retention of the pad 1 under the foot.

It should also be noted that, thanks to a reduction in the thickness e of the base 15 of the insert 11 compared to a flat insert having a thickness offering the same pressure distribution capacity (same volume of material per unit of surface), the insert 11 more closely follows the anatomy of the metatarsal zone having a double convex shape (convex longitudinally and transversely). Indeed, since the studs 14 are not linked together, they do not increase the bending resistance of the insert 11. It is therefore the thickness e of the flat base 15 that defines the flexural strength and thus the ability of the insert to conform to the shape of the plantar pad in the region of the metatarsal heads.

In addition, wearing a pad under the forefoot adds a significant amount of soft material to this area. This changes the orientation of the foot relative to the ground (by raising the forefoot), as well as the feel of the ground when loading with the body weight in a static situation and in motion. The feeling of the ground perceived by the user is no longer direct but delayed in time and can be modified by shear deformations in the bulk of the pad. The addition of the pad has the consequence of disturbing the user's balance while walking, and of decreasing his capacity to regulate his posture within his cone of stability, in particular when support is carried by a single foot during the propulsion phase. It should be noted that the user's balance can be affected by many external factors, such as the nature of the ground, which can vary in hardness (e.g. sand or grass), gusts of wind, and the presence of grips on the shoe soles. However, the majority of people who need to wear protection under their metatarsal heads are senior persons who may already have poor or declining stability. Thus, a pad 1 having a flat base 15 scaled by studs 14 has the advantage of being the least destabilizing possible during walking movements, due to a reduction in thickness under load, compared to a pad having the same pressure distribution characteristics.

It will be apparent to those skilled in the art that the present invention is susceptible of various alternatives and applications. In particular, the invention is not limited to an insert having studs. Indeed, the insert may be flat, knowing that such an insert may also perform the pressure distribution function. The insert may also be made of a viscoelastic material that can be attached directly to the strap 2, without the need to wrap the insert in a pocket.

The insert 11 may have studs of other shapes. The parameters to be considered for the layer including the studs are the height h of the studs, the distance d2 between the studs and the filling rate of this layer, or the thickness, referred to in the following as the "equivalent thickness" of the volume of material distributed in the studs per unit of area, when this volume is distributed in a full layer. According to an embodiment, the height of the studs is between 1 and 2 mm and the filling ratio of the layer including the studs is between 20 and 40%, or the equivalent thickness of the studs is between 20 and 40% of the height of the studs.

The height h and shape of the studs 14, as well as the distance between the studs 14, are not necessarily uniform over the entire insert 11, but may be defined locally according to the needs, in particular of pressure distribution and thickness under load. For example, it may be found that the pressure exerted on the ground by the head of the first two metatarsals is higher than that exerted by the head of the fifth metatarsal. The equivalent thickness of the studs 14 may therefore become thinner along a line from the head of the first metatarsal to the head of the fifth metatarsal.

Furthermore, the camber and therefore the rotation of the brace 22 to fix it to the pad 1 can be omitted, without affecting the comfort of the device, by adjusting the position of the brace 22 in relation to the strap 2 and to the pad 1.

In some applications, it may be desirable to obtain better adhesion of the insert to the skin. In this case, all or only a portion of the inner fabric piece 13 may be omitted. Similarly, the use of the support device may be combined with wearing a sock. In this context, a better adhesion of the insert 11 to a sock covering the foot may be sought. A portion, in particular a central portion, of the outer fabric piece 12 may also be omitted.

A piece of fabric may also be embedded in the insert 11, this piece of fabric being used in particular to secure the strap 2 to the insert 11, for example by means of seams.

The invention claimed is:

1. A method of fabricating a device for protecting a plantar pad of a foot, comprising:
   providing a pad including a viscoelastic material, configured to be held on skin of a plantar region, and to cover all metatarsal heads and metatarsophalangeal joints of the foot, the pad comprising a distal edge and lateral edges,
   providing an elastic strap comprising a transverse portion and a longitudinal portion, the longitudinal portion of the elastic strap having a distal edge and a lateral edge, the transverse portion of the elastic strap having a distal edge,
   attaching the elastic strap to the lateral edges of the pad, and fixing the distal edge of the longitudinal portion of the elastic strap to the distal edge of the pad along a securing line, so that the elastic strap forms a brace configured to pass between a big toe and an adjacent toe of the foot,
   the distal edge of the transverse portion of the elastic strap delimiting, with the pad and the lateral edge of the longitudinal portion of the elastic strap, an aperture for passage of second to fifth toes, wherein
   the lateral edge of the longitudinal portion of the elastic strap has a length between 40% and 60% of a length of the distal edge of the transverse portion of the elastic strap,
   the distal edge of the transverse portion of the elastic strap and the lateral edge of the longitudinal portion of the elastic strap have, in an unstretched flat state, rectilinear portions forming an angle between 75° and 100° with each other, and
   the length of the distal edge of the transverse portion of the elastic strap is between 55% and 65% of a length of the transverse portion,
   the method further comprising, before fixing the distal edge of the longitudinal portion of the elastic strap to the distal edge of the pad along the securing line, rotating the distal edge of the longitudinal portion of the elastic strap so that the brace is fixed to the pad forming a camber, keeping an opening for the passage of the big toe of the foot open, wherein
   size of the camber is determined by an amplitude of rotation of the distal edge of the longitudinal portion of the elastic strap relative to the distal edge of the pad before attaching the distal edge of the longitudinal portion of the elastic strap to the distal edge of the pad along the securing line,
   the amplitude of rotation of the distal edge of the longitudinal portion of the elastic strap relative to the distal edge of the pad is between 80° and 100° within a plane of the pad when laid flat at the securing line, and
   location of the securing line of the distal edge of the longitudinal portion of the elastic strap to the distal edge of the pad increases angle between the rectilinear portions of the distal edge of the transverse portion of the elastic strap and the lateral edge of the longitudinal portion of the elastic strap such that in an unstretched flat state, after securing the distal edge of the longitudinal portion of the elastic strap to the distal edge of the pad, the rectilinear portions form the angle between 75° and 100° with each other.

2. The method of claim 1, wherein the pad is configured to extend in a plane where the pad is intended to be held on the skin of the plantar region.

3. The method of claim 1, wherein the longitudinal portion has at a distal edge of the longitudinal portion a width of 1.5 cm±20%.

4. The method of claim 1, wherein the pad comprises an outer fabric piece joined with an inner fabric piece to form a pocket in which an insert is housed.

5. The method of claim 4, wherein the outer fabric piece has a thickness between 0.5 mm and 0.8 mm, and the inner fabric piece has a thickness between 0.1 mm and 0.5 mm.

6. The method of claim 4, wherein the insert is bonded to the outer fabric piece.

7. The method of claim 4, wherein the insert comprises a flat base, the flat base having an upper face on a foot-side and a lower face opposite the upper face, and studs on the upper face of the flat base.

8. The method of claim 7, wherein the flat base has a thickness between 1.4 mm and 2 mm, and the studs extend over a height above the flat base between 1.3 mm and 1.7 mm and have a total volume per unit of area equivalent to that of a flat layer having ⅓ of the height±10%.

9. The method of claim 7, wherein the studs have a spherical cap shape with a diameter of 4 mm+0.2 mm, and are spaced apart from each other in 0°, 60° and 120° directions by a distance of 5 mm+0.2 mm.

10. The method of claim 1, wherein the viscoelastic material is based on a polydimethylsiloxane silicone gel composition.

11. A method of fabricating a device for protecting a plantar pad of a foot, the method comprising:
   providing a pad that includes a viscoelastic material and is configured to be held on skin of a plantar region and to cover all metatarsal heads and metatarsophalangeal joints of the foot, the pad having a distal edge and opposite lateral edges;
   providing an elastic strap having i) a transverse portion terminating in a distal edge and ii) a longitudinal portion forming a brace terminating in a distal edge and a lateral edge, wherein, in an unstretched flat state,
      a) the distal edge of the transverse portion and the lateral edge of the longitudinal portion define rectilinear portions forming a first angle,
      b) a length of the lateral edge of the longitudinal portion is 40% to 60% of a length of the distal edge of the transverse portion, and
      c) a length of the distal edge of the transverse portion is 55% to 65% of a length of the transverse portion;
   attaching the transverse portion of the elastic strap to lateral edges of the pad;
   determining a securing line on the distal edge of the pad such that fixing the distal edge of the longitudinal portion along said securing line requires rotating the distal edge of the longitudinal portion by an amplitude of 80° to 100° within a plane of the pad when laid flat, and results in increasing the first angle to a second angle between 75° and 100°; and
   fixing the distal edge of the longitudinal portion to the distal edge of the pad along the securing line, wherein the fixing requires the rotating the distal edge of the longitudinal portion, thereby fixing the brace to the pad forming a camber that keeps open an opening for passage of the big toe of the foot; wherein
   the distal edge of the transverse portion of the elastic strap delimits, with the pad and the lateral edge of the longitudinal portion of the elastic strap, an aperture for passage of the second to fifth toes, and size of the camber is dependent on the amplitude of 80° to 100°.

12. The method of claim 11, wherein the pad is configured to extend in a plane where the pad is intended to be held on the skin of the plantar region.

13. The method of claim 11, wherein the longitudinal portion has at a distal edge of the longitudinal portion a width of 1.5 cm±20%.

14. The method of claim 11, wherein the pad comprises an outer fabric piece joined with an inner fabric piece to form a pocket in which an insert is housed.

15. The method of claim 14, wherein the outer fabric piece has a thickness between 0.5 mm and 0.8 mm, and the inner fabric piece has a thickness between 0.1 mm and 0.5 mm.

16. The method of claim 14, wherein the insert is bonded to the outer fabric piece.

17. The method of claim 14, wherein the insert comprises a flat base, the flat base having an upper face on a foot-side and a lower face opposite the upper face, and studs on the upper face of the flat base.

18. The method of claim 17, wherein the flat base has a thickness between 1.4 mm and 2 mm, and the studs extend over a height above the flat base between 1.3 mm and 1.7 mm and have a total volume per unit of area equivalent to that of a flat layer having ⅓ of the height±10%.

19. The method of claim 17, wherein the studs have a spherical cap shape with a diameter of 4 mm±0.2 mm, and are spaced apart from each other in 0°, 60° and 120° directions by a distance of 5 mm±0.2 mm.

20. The method of claim 11, wherein the viscoelastic material is based on a polydimethylsiloxane silicone gel composition.

\* \* \* \* \*